United States Patent [19]
Hartwig et al.

[11] Patent Number: 6,057,456
[45] Date of Patent: May 2, 2000

[54] TRANSITION METAL-CATALYZED PROCESS FOR PREPARING ALPHA-ARYLATED CARBONYL-CONTAINING COMPOUNDS

[75] Inventors: John F. Hartwig, New Haven, Conn.; Blake C. Hamann, Winchester, Mass.

[73] Assignee: Yale University, New Haven, Conn.

[21] Appl. No.: 09/173,527

[22] Filed: Oct. 15, 1998

Related U.S. Application Data

[60] Provisional application No. 60/062,212, Oct. 16, 1997.

[51] Int. Cl.[7] .................. C07D 207/30; C07D 307/02; C07C 255/07; C07C 303/16; C07C 45/37
[52] U.S. Cl. .................. 548/540; 558/371; 549/70; 549/483; 568/312; 568/317
[58] Field of Search .................. 558/371; 568/312; 568/317; 548/540; 549/70, 483

[56] References Cited

U.S. PATENT DOCUMENTS

| | | | |
|---|---|---|---|
| 5,576,460 | 11/1996 | Buchwald et al. | 564/386 |
| 5,847,166 | 12/1998 | Buchwald et al. | 549/355 |

OTHER PUBLICATIONS

Muratake, H. et al., Palladium–Catalyzed Intramolecular α–Arylation of Aliphatic Ketones, Tetrahedron Letters, vol. 38, No. 43, pp. 7581–7582, 1997.

Stille, J.K., The Palladium–Catalyzed Cross–Coupling Reactions of Organotin Reagents with Organic Electrophiles, Angew, Chem., Int. Ed. Engl., 25:508–524 (1986).

Miyaura, N. et al., Palladium–Catalyzed Cross–Coupling Reactions of Organoboron Compounds, Chem. Rev., 95:2457–2483 (1995).

Negishi, E., Palladium– or Nickel–Catalyzed Cross Coupling. A New Selective Method for Carbon–Carbon Bond Formation, Acc. Chem. Res., 15:340–348 (1982).

Kosugi, M. et al., Arylation and 1–Alkenylation on α–Position of Ketones via Tributyltin Enolates Catalyzed by Palladium Complex, Bull. Chem. Soc. Jpn., 57:242–246 (1984).

Carfagna, C. et al., Palladium–Catalyzed Coupling Reactions of Aryl Triflates or Halides with Ketene Trimethylilyl Acetals. A New Route to Alkyl 2–Arylalkanoates, J. Org. Chem., 56:261–263 (1991).

Durandetti, M. et al., Nickel–Catalyzed Direct Electrochemical Cross–Coupling between Aryl Halides and Activated Alkyl Halides, J. Org. Chem. 61:1748–1755 (1996).

Fauvargue, J.F. et al., Catalysis Of The Arylation Of The Reformatsky Reagent By Palladium Or Nickel Complexes, Synthesis Of Aryl Acid Esters, J. Organomet. Chem., 177:273–281 (1979).

Barton, D.H.R. et al., Copper Catalyzed O–Phenylation Of Phenols And Enols By Pentavalent Organobismuth Compounds, Tet. Letters, 27:3619–3622 (1986).

Barton, D.H.R. et al., Application of Aryllead(iv) Derivatives to the Preparation of 3–Aryl–4–hydroxy–1–benzopyran–2–ones, J. Chem. Soc., Perkin Trans. 1:1365–1375 (1992).

Satoh, T. et al., Palladium–Catalyzed Regioselective Mono– and Diarylation Reactions of 2–Phenylphenols and Napthols with Aryl Halides, Communications, Angew. Chem. Int. Ed. Engl. 1997, 36, No. 16, pp. 1740–1742.

*Primary Examiner*—Joseph McKane
*Assistant Examiner*—Ebenezer Sacket
*Attorney, Agent, or Firm*—Todd E. Garabedian; Wiggin & Dana

[57] ABSTRACT

The present invention is directed to a process for preparing alpha-arylated carbonyl-containing compounds, comprising the steps of reacting a compound having at least one carbonyl group with an arylating compound in the presence of a base and a transition metal catalyst under reaction conditions effective to form an alpha-arylated carbonyl-containing compound, the transition metal catalyst comprising a Group 8 metal and at least one chelating ligand selected from the group consisting of unsaturated Group 15 heterocycles, Group 15-substituted metallocenes, Group 15-substituted alkanes, Group 15-substituted arylenes, and combinations thereof. The process of the present invention simplifies the preparation of commercially significant organic alpha-aryl carbonyl-containing compounds, particularly for use in the pharmaceutical and polymer industries.

22 Claims, No Drawings

TRANSITION METAL-CATALYZED PROCESS FOR PREPARING ALPHA-ARYLATED CARBONYL-CONTAINING COMPOUNDS

CROSS-REFERENCE TO RELATED APPLICATIONS

This application claims the benefit of U.S. Provisional Application No. 60/062,212 filed Oct. 16, 1997.

STATEMENT OF GOVERNMENT SUPPORT

This application was made with United States Government support under Award Number 1-R29-GM382-01 from the National Institutes of Health. The U.S. Government has certain rights in this invention.

BACKGROUND OF THE INVENTION

1. Field of the Invention

This invention relates to a general process for alpha-arylation of carbonyl-containing compounds, and more particularly to a general process for synthesizing alpha-arylated carbonyl-containing compounds from arylating compounds and carbonyl containing compounds using a transition metal catalyst.

2. Description of the Related Art

The palladium-catalyzed coupling to form C—C bonds between aryl and vinyl halides or triflates and a carbon nucleophile is one of the most widely used transition metal-catalyzed reactions. (Stille, J. K. *Angew. Chem., Int. Ed. Engl.*, 25:508–524 (1986); Miyaura, N. et al., *Chem. Rev.*, 95:2457–2483 (1995); Negishi, E. *Acc. Chem. Res.*, 15:340–348 (1982)). The related cross-coupling reactions involving ketone enolates as the nucleophile are also very important commercially. However, this class of cross-coupling reactions has been limited to tin enolates, silyl-enol ethers in combination with tin fluoride, intramolecular examples, or examples with acid ketones and metal ion catalysts in low yields (Kosugi, M. et al., *Bull. Chem. Soc. Jpn.*, 57:242–246 (1984)).

Many transition metal-catalyzed approaches to ketone arylation using pre-formed main group enol ethers (Carfagna, C. et al., *J. Org. Chem.*, 56:261–263 (1991); Durandetti, M. et al., *J. Org. Chem.* 61:1748–1755 (1996); Fauvargue, J. F. et al., *J. Organomet. Chem.*, 177:273–281 (1979)) or bismuth or lead reagents (Barton, D. H. R. et al., *Tet. Letters*, 27:3619–3522 (1986); Barton, D. H. R. et al., *J. Chem. Soc., Perkin Trans.* 1:1365–1375 (1992)) have been investigated. However, use of toxic main-group reagents, low product yields, and multi-step preparation of compounds make these procedures particularly difficult to exploit commercially. In addition, arylation using a metal halide in the absence of a chelating ligand has been shown (Satoh et al., *Angew. Chem. Int. Ed. Engl.* 36:1740–1741 (1997)); however, the yield of product is unacceptably low for commercial purposes.

It would be advantageous to prepare alpha-aryl carbonyl-containing compounds from arylating compounds such as aryl halides and/or aryl sulfonates because aryl halides are generally inexpensive and readily available, while aryl sulfonates are easily prepared from phenols. However, to date, the simple direct reaction of an arylating compound and a carbonyl-containing compound (such as a ketone) with base in the presence of a transition metal catalyst has not been reported.

In view of the above, a need exists for a general and efficient process of synthesizing alpha-aryl carbonyl-containing compounds. The discovery and implementation of such a process would simplify the preparation of commercially significant organic alpha-aryl carbonyl-containing compounds and would enhance the development of novel pharmacologically active compounds. The present invention is believed to be an answer to that need.

SUMMARY OF THE INVENTION

In one aspect, the present invention is directed to a process for preparing an alpha-arylated carbonyl-containing compound, comprising reacting a compound having at least one carbonyl group with an arylating compound in the presence of a base and a transition metal catalyst under reaction conditions effective to form the alpha-arylated carbonyl-containing compound, the transition metal catalyst comprising a Group 8 metal and at least one chelating ligand selected from the group consisting of unsaturated Group 15 heterocycles, Group 15-substituted metallocenes, Group 15-substituted alkanes, Group 15-substituted arylenes, and combinations thereof.

In another aspect, the present invention is directed to a process for preparing an alpha-arylated carbonyl-containing compound, comprising reacting a compound having at least one carbonyl group with an arylating compound in the presence of a base and a transition metal catalyst under reaction conditions effective to form said alpha-arylated carbonyl-containing compound, said transition metal catalyst selected from the group consisting of dichloro-[1,1'-bis(diphenylphosphino)-ferrocene]palladium (II), dichloro[1,1'-bis(di-o-tolylphosphino)ferrocene]palladium (II), and combinations thereof.

These and other aspects will become apparent upon reading the following detailed description of the invention.

DETAILED DESCRIPTION OF THE INVENTION

It now has been surprisingly found, in accordance with the present invention, that a solution is provided to the problem of providing a general and efficient process of synthesizing alpha-arylated and vinylated carbonyl-containing compounds from a starting material having at least one carbonyl group, and an arylating compound. The present inventors have solved this problem by utilizing reaction conditions that include a base and a transition metal catalyst having a Group 8 metal and at least one chelating ligand selected from unsaturated Group 15 heterocycles, Group 15-substituted metallocenes, Group 15-substituted alkanes, Group 15-substituted arylenes, and combinations thereof. In one embodiment, the catalyst comprises a palladium complex of 1,1'-bis(diphenylphosphino)-2,2'-binapthyl (BINAP), 1,1'-bis(diphenylphosphino)ferrocene (DPPF), or 1,1'-bis(di-o-tolylphosphino)ferrocene (DTPF). The process of the present invention provides a general process for production of alpha-arylated or -vinylated carbonyl-containing compounds, a class of compounds which are particularly significant in the development of pharmacologically active compounds and production of polymers and oligomers.

As defined herein, "alpha-carbon" refers to the carbon atom directly adjacent to a carbonyl (C=O) group in an organic molecule. The phrases "alpha arylation", "alpha arylating", and "alpha arylated" refer to attachment of an aryl group onto the alpha carbon of an organic compound. The terms "aryl" and "aryl group" are defined as a compound or compounds whose molecules have the ring structure characteristic of benzene, naphthalene, phenanthroline, anthracene, and the like.

The process of the present invention is directed to the synthesis of alpha-arylated and -vinylated carbonyl-containing compounds, particularly alpha-arylated ketones. The process of the invention comprises reacting a compound having at least one carbonyl (C=O) group with an arylating compound in the presence of a base and a transition metal catalyst under reaction conditions effective to form an alpha-arylated carbonyl-containing compound. The transition metal catalyst generally comprises a Group 8 metal and at least one chelating ligand selected from the group consisting of unsaturated Group 15 heterocycles, Group 15-substituted metallocenes, Group 15-substituted alkanes, Group 15-substituted arylenes, and combinations thereof.

More specifically, the process of this invention can be represented by Scheme I:

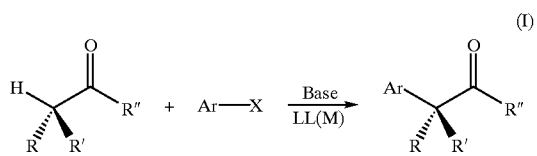
(I)

Briefly, in Scheme I, an arylating compound (Ar-X) is reacted with a carbonyl-containing compound in the presence of a base, a chelating ligand (LL), and a Group 8 metal (M) to form an alpha-arylated carbonyl-containing compound. This reaction and each of the components are described in more detail below.

The arylating compound used in the process of the present invention may be any arylating compound of the formula (II):

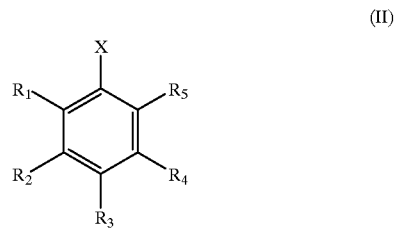
(II)

In formula (II), X may be any halide atom (F, Cl, Br, I), or any sulfur-containing leaving group (e.g., triflate, sulfonate, tosylate, and the like) known in the art. Bromides are especially preferred in the process of the present invention. $R_1$, $R_2$, $R_3$, $R_4$, and $R_5$ are independently selected from H; CN; alkyl, such as methyl, ethyl, propyl, n-butyl, t-butyl, and the like; formyl; $CF_3$; $CCl_3$; $C_6H_5$; amide such as $C(O)N(CH_3)_2$, $C(O)N(CH_2CH_3)_2$, $C(O)N(CH_2CH_2CH_3)_2$, and the like; acyl, such as $C(O)$—$C_6H_5$, and the like; ester, aryl, alkoxy, amino, and the like.

Preferred arylating compounds used in the process of the invention include aryl halides such as bromobenzene, 4-bromo-benzonitrile, 4-bromo-t-butyl benzene, 3-bromo-methoxy benzene, 2-bromo toluene, para-formyl phenyl bromide, p-$CF_3$ phenyl bromide, p-phenyl phenyl bromide, p-$C(O)N(CH_2CH_3)_2$ phenyl bromide, and p-$C(O)$—$C_6H_5$ phenyl bromide.

According to the process of the invention, compounds containing at least one carbonyl group include any carbonyl-containing compound that possesses an alpha-carbon. The structure of preferred set of carbonyl-containing compounds is

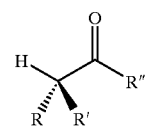

where R and R' are independently selected from hydrogen, alkyl or aryl; and R" is hydrogen, aryl or alkyl such as t-butyl. Preferred aryl groups for R" include phenyl, pyrrole, N-substituted pyrrole, furan, thiophene, and the like.

Exemplary carbonyl-containing groups include ketones, amides, esters, carboxylic acids, thioesters, amidines, anhydrides; β-dicarbonyl compounds such as malonates, acetoacetates, β-diketones, and the like; and α-dicarbonyl compounds, such as α-diketones, α-ketoesters, α-ketamides, and the like. Particularly useful carbonyl-containing compounds include alkyl aryl ketones, such as acetophenone, propiophenone, isobutyrophenone, and dialkyl ketones, such as acetone and diethyl ketone.

The base shown in Scheme I is required for the process of the present invention. Any base may be used so long as the process of the invention proceeds to the alpha-aryl product. It may be important in this regard that the base does not displace all of the chelating ligands on the catalyst. Nuclear magnetic resonance, infrared, and Raman spectroscopies, for example, are useful in determining whether the chelating ligands remain bonded to the Group 8 metal or whether the ligands have been displaced by the base.

Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethylammonium hydroxide and tetraethylammonium hydroxide; diaza organic bases, such as 1,8-diazabicyclo[5.4.0]-undec-7-ene and 1,8-diazabicyclo-[2.2.2.]-octane, and silyl compounds such as potassium hexamethyldisilazide ($KN(Si(CH_3)_3)_2$). Preferably, the base is an alkali alkoxide or a silyl-containing compound.

The quantity of base which is used can be any quantity hich allows for the formation of the alpha-aryl product. Preferably, the molar ratio of base to arylating compound ranges from about 1:1 to about 3:1, and more preferably between about 1:1 and 2:1.

The catalyst, designated (LL)M in Scheme I, is characterized as comprising a metal atom or ion (M) and at least one or more chelating ligands (LL). The metal atom or ion is required to be a Group 8 transition metal, that is, a metal selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal.

The chelating ligand may be a neutral molecule or charged ion. A chelating ligand possesses a plurality of coordination sites, typically two, three, or four. Preferably, the chelating ligand is a bidentate ligand, that is, one having two coordination sites. The chelating ligand is also required to contain at least one element from Group 15 (formerly Known as Group VB) of the Periodic Table, preferably, at least one element of nitrogen, phosphorus, or arsenic, and more preferably nitrogen or phosphorus. If only one of the Group 15 elements is present, then at least a second chelating element is required, for example, oxygen or sulfur. more specifically, the chelating ligand is selected from the group consisting of Group 15-substituted arylenes, Group 15-substituted metallocenes, unsaturated Group 15 heterocycles, and Group 15-substituted alkanes.

The term "Group 15-substituted arylenes" as used herein includes aromatic compounds substituted with at least one Group 15-containing moiety, preferably, at least one dialkyl or diaryl Group 15 moiety or hybrid thereof. The aromatic compound can be a single ring, fused ring, or multiple ring assembly. Other chelating elements, such as oxygen or sulfur, may be present. Non-limiting examples of Group 15-substituted arylenes which are chelating and beneficially employed in the process of this invention include 1,2-bis(diphenylphosphino)benzene, 1,1'-bis(diphenylphosphino)-2,2'-binaphthyl, 1-(dimethylarsino)-2-bis[(dimethylamino)phosphino)]benzene, 1,2-bis(dimethylarsino)benzene, 5–10-dihydro-5,10-diphenyl-5-phospha-10-arsa-anthracene, 2-diphenylphosphino-N,N-dimethylaniline, 1,8-bis(diphenylphosphino)naphthalene, 2,2-bis(diphenylphosphino)diphenyl ether, 4,5-bis(diphenylphosphino)-9,9-dimethyl)xanthene, and 1,1'-bis(di-p-tolylphosphino)-2,2'-binaphthyl, 1-diphenylphosphino-1'-dimethylamino-2,2'-binaphthyl, 1-dicyclohexylphosphino-1'-dimethylamino-2,2'-binaphthyl, 1-di-t-butylphosphino- 1'-dimethylamino-2,2'-binaphthyl, 1-di-i-propylphosphino-1'-dimethylamino-2,2'-binaphthyl, 1-diphenylphosphino-1'-methoxy-2,2'-binaphthyl, 1-dicyclohexylphosphino-1'-methoxy-2,2'-binaphthyl, 1-di-t-butylphosphino-1'-methoxy-2,2'-binaphthyl, 1-di-i-propylphosphino-1'-dimethylamino-2,2'-binaphthyl, 1-diphenylphosphino-1'-dimethylamino-2,2'-biphenyl, 1-dicyclohexylphosphino-1'-dimethylamino-2,2'-biphenyl, 1-di-t-butylphosphino-1'-dimethylamino-2,2'-biphenyl, 1-di-i-propylphosphino-1'-dimethylamino-2,2'-binaphthyl, 1-diphenylphosphino-1'-methoxy-2,2'-biphenyl, 1-dicyclohexylphosphino-1'-methoxy-2,2'-biphenyl, 1-di-t-butylphosphino-1'-methoxy-2,2'-biphenyl, and 1-di-i-propylphosphino-1'-dimethylamino-2,2'-binaphthyl. Analogous diamino, diphosphino, and diarsino compounds and hybrids thereof are also suitable. Preferably, the Group 15-substituted arylene is a Group 15-substituted $C_{4-20}$ arylene, more preferably, a Group 15-substituted binaphthyl compound, more preferably, 1,1'-bis(diphenylphosphino)-2,2'-binaphthyl (BINAP) or 1,1'-bis(di-p-tolyl-phosphino)-2,2'-binaphthyl.

The term "Group 15-substituted metallocenes" as used herein includes metallocenes which are substituted with at least one Group 15-containing moiety, preferably at least one dialkyl or diaryl Group 15 moiety or hybrid thereof. Other chelating elements, for example, oxygen or sulfur, may be present. The metallocene itself comprises a transition metal atom or ion which is bonded to one or more $C_{4-8}$ multiply unsaturated hydrocarbon ring compounds. Suitable non-limiting examples of transition metal atoms in the metallocene include iron, titanium, vanadium, chromium, manganese, cobalt, nickel, molybdenum, and ruthenium. Preferably, the transition metal atom in the metallocene is iron. The $C_{4-8}$ multiply unsaturated hydrocarbon ring compounds suitably include cyclobutadiene, cyclopentadienyl, benzene, cycloheptatrienyl, and cyclooctatetraene. Representative metallocenes include ferrocene, ruthenocene, bis(benzene)chromium, bis(benzene)-molybdenum, bis(benzene)tungsten, and cobaltocenium. Non-limiting examples of ligands which classify as chelating Group 15-substituted metallocenes include 1,1'bis(diphenylphosphino)ferrocene, 1,1'-bis(di-o-tolylphosphino)ferrocene (DTPF), 1-diphenylphosphino-2-(1-dimethylamino)ethyl ferrocene, 1-diphenylarsino-1'-diphenyl-phosphino ferrocene, 1-diphenylphosphino-2-(1-diphenylphosphino)ethyl ferrocene, 1-diphenylphosphino-2-(1-di-t-butylphosphino)ethyl ferrocene, 1-diphenylphosphino-2-(1-dicyclohexylphosphino)ethyl ferrocene, 1-dicyclohexylphosphino-2-(1-diphenylphosphino)ethyl ferrocene, 1-dicyclohexylphosphino-2-(1-dicyclohexylphosphino)ethyl ferrocene, 1-dicyclohexylphosphino-2-(1-dimethylamino)ethyl ferrocene, 1-di-t-butylphosphino-2-(1-dimethylamino)ethyl ferrocene, 1-di-i-propylphosphino-2-(1-dimethylamino) ethyl ferrocene, 1-diphenylphosphino-2-(1-dimethylamino) ethyl ferrocene, 1-[2-(diphenylphosphino)ferrocenyl]ethyl methyl ether, 1-[2-(dicyclohexylphosphino)ferrocenyl]ethyl methyl ether, 1-[2-(di-i-propylphosphino)ferrocenyl]ethyl methyl ether, and 1-[2-(di-t-butylphosphino)ferrocenyl] ethyl methyl ether. Analogous phosphine and amine substituted derivatives of the aforementioned metallocenes may also be employed. Preferably, the Group 15-substituted metallocene is a Group 15-substituted ferrocene, more preferably, 1,1'-bis(diphenylphosphino)ferrocene (DPPF) or 1,1'-bis(di-o-tolylphosphino)ferrocene (DTPF).

The term "unsaturated Group 15 heterocycles" as used herein includes any unsaturated single ring, multiple ring assembly, or fused ring system which comprises at least one Group 15 heteroatom. Preferably, the heteroatom is nitrogen. Chelating atoms outside of Group 15, such as oxygen or sulfur, may also be present. Non-limiting examples of unsaturated Group 15 heterocycles which are chelating and which can be beneficially employed in the process of the present invention include bipyridine, alkoxypyridine, imidazole, pyrazole, pyrimidine, pyridazine, purine, and quinazoline. Preferably, the unsaturated Group 15 heterocycle is an unsaturated $C_{5-15}$ Group 15 heterocycle, more preferably bipyridine or alkoxypyridine.

The term "Group 15-substituted alkanes" as used herein includes alkanes, preferably $C_{2-5}$ alkanes, and more preferably $C_{3-4}$ alkanes, which are substituted with at least one Group 15-containing moiety, preferably, a dialkyl or diaryl Group 15 moiety or hybrid thereof. Non-limiting examples of ligands which classify as chelating Group 15-substituted alkanes and which may be beneficially employed in the process of the present invention include 1,3-bis(diphenylphosphino)propane, 1,4-bis(diphenylphosphino)butane, 1,3-bis(diphenylarsino)propane, 1,4-bis(diphenylarsino)butane, 1-(diphenylphsophine)-2-(N,N-dimethyl)ethane, 1-(diphenyphosphino)-3-(N,N-dimethyl)propane, and 1-(diphenylarsino)-2-(diphenylphosphino)ethane.

In one preferred embodiment, the chelating ligand is a bidentate ligand containing at least one phosphorous atom. More preferably, the chelating ligand is a bidentate ligand selected from the group consisting of phosphorous-substituted arylenes and phosphorous-substituted metallocenes. Most preferably, the ligand is 1,1'-bis(diphenylphosphino)-2,2'-binapthyl (BINAP), 1,1'-bis(di-p-tolyphosphino)-2,2'-binapthyl(Tol-BINAP), or 1,1'-bis(diphenylphosphino)ferrocene (DPPF).

Many of the aforementioned metal catalysts which are beneficially employed in the process of this invention can be represented by the following formula:

$$(LL)_{1 \text{ or } 2} MX_Y$$

wherein (LL) is the chelating ligand, M is the Group 8 transition metal, each X is independently a monovalent anionic ligand, including for example a halide, such as chloride or bromide; a carboxylate, such as acetate; or an alkyl sulfonate, such as triflate; or X is a divalent anionic ligand, such as sulfonate or carbonate; and wherein y represents the total number of anionic ligands X required to balance charge, typically from 0 to about 4. It is to be understood that any of the chelating ligands described earlier may be used in the above formula. Non-limiting examples of suitable transition metal complexes include dichloro-[1,1'-bis(diphenylphosphino)ferrocene]palladium (II), [1,1'-bis (di-o-tolylphosphino)ferrocene]palladium (II), dichloro-[1,1 (1'-bis(diphenylphosphino)-2,2'-binapthyllpalladium (II), dichloro-[1,2-bis(diphbenzene]platinum (II), 1,2-bis [(diphenylphosphino) benzene]platinum (II) acetate, dichloro-[1-diphenylphosphino-2-(1-dimethylamino) ethylferrocene]palladium (II), and analogous complexes containing bidentate ligands mentioned hereinbefore with iron, cobalt, nickel, ruthenium, rhodium, osmium, and iridium as the metal component.

Methods for preparing the aforementioned catalysts are known to those skilled in the art. For a description of general synthetic techniques, see *Inorganic Synthesis: Reagents for Transition Metal Complex and Organometallic Systems*; R. J. Angelici, Ed., Wiley-Interscience: New York, 1990, Vol. 28, pp. 77–135 (Chapter 2), incorporated herein by reference, wherein representative preparations of Group 8 complexes containing chelating amine, phosphine, and arsine ligands are taught.

As an alternative embodiment of this invention, the catalyst may be anchored or supported on a catalyst support, including a refractory oxide, such as silica, alumina, titania, or magnesia; or an aluminosilicate clay, or molecular sieve or zeolite; or an organic polymeric resin.

Heretofore, the transition metal catalyst has been described as comprising a transition metal and a chelating ligand. It is not precisely known, however, whether the chelating ligand is bound to the transition metal during the entire process of this invention or whether the chelating ligand is in a labile or non-bonded configuration relative to the transition metal during part or all of the process. Generally, it is believed that the chelating ligand is bonded through the Group 15 element to the transition metal; however, such a theory should not be binding upon the invention in any manner. Modern analytical techniques, such as nuclear magnetic resonance spectroscopy ($^{13}C$, $^1H$, $^{31}p$), infrared and Raman spectroscopies, and X-ray diffraction, may assist in the determination of initial catalyst structure and changes in structure throughout the process.

The transition metal catalyst may be synthesized first and thereafter employed in the arylation process. Alternatively, the catalyst can be prepared in situ in the arylation reaction mixture. If the latter mixture is employed, then a Group 8 catalyst precursor compound and the desired chelating ligand are independently added to the reaction mixture wherein formation of the transition metal catalyst occurs in situ. Suitable precursor compounds include alkene and diene complexes of the Group 8 metals, preferably, (dibenzylidene)acetone (dba) complexes of the Group 8 metals, as well as, monodentate phosphine complexes of the Group 8 metals, and Group 8 carboxylates. In the presence of the chelating ligand, such as DPPF or BINAP, in situ formation of the transition metal catalyst occurs. Non-limiting examples of suitable precursor compounds include [bis-(dibenzylidene)acetone]palladium (0), tetrakis-(triphenylphosphine)-palladium (0), tris-[(dibenzylidene) acetone]palladium (0), tris-[(dibenzylidene) acetone] dipalladium (0), palladium acetate, and the analogous complexes of iron, cobalt, nickel, ruthenium, rhodium, osmium, iridium, and platinum. Any of the aforementioned catalyst precursors may include a solvent of crystallization. Group 8 metals supported on carbon, preferably, palladium on carbon, can also be suitably employed as a precursor compound. Preferably, the catalyst precursor compound is bis-[(dibenzylidene)acetone]palladium(0).

The quantity of transition metal catalyst which is employed in the process of this invention is any quantity which promotes the formation of the alpha-aryl product. Generally, the quantity is a catalytic amount, which means that the catalyst is used in an amount which is less than stoichiometric relative to the unsaturated organic sulfonate. Typically, the transition metal catalyst ranges from about 0.01 to about 20 mole percent, based on the number of moles of the carbonyl-containing compound used in the reaction. Preferably, the quantity of transition metal catalyst ranges from about 1 to about 10 mole percent, and more preferably from about 3 to about 8 mole percent, based on the moles of the carbonyl-containing compound.

The process described herein may be conducted in any conventional reactor designed for catalytic processes. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the carbonyl-containing compound, arylating compound, base, and catalyst are mixed in batch, optionally with a solvent, and the resulting mixture is maintained at a temperature and pressure sufficient to prepare the alpha-arylated product.

Any solvent can be used in the process of the invention provided that it does not interfere with the formation of the alpha-aryl product. Both aprotic and protic solvents are acceptable. Suitable aprotic solvents include, but are not limited to, aromatic hydrocarbons, such as toluene and xylene, chlorinated aromatic hydrocarbons, such as dichlorobenzene; and ethers, such as tetrahydrofuran. Suitable protic solvents include, but are not limited to, water and aliphatic alcohols, such as ethanol, isopropanal, and cyclohexonal, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of solvent may also be suitable, as determined by the specific process conditions and by the skilled artisan.

Generally, the reagents may be mixed together or added to a solvent in any order. No special effort is required to eliminate air from the reaction mixture, unless one or more of the reagents are particularly air-sensitive. If it is desirable or necessary to remove air, the solvent and reaction mixture can be sparged with a non-reactive gas, such as nitrogen, helium, or argon. The process conditions can be any operable conditions which yield the desired alpha-aryl product. Beneficially, the reaction conditions for this process are mild. For example, a preferred temperature for the process of the present invention ranges from about ambient, taken as about 22° C., to about 150° C., and preferably, from about 80° C. to about 110° C. The process may be run at subatmospheric pressures if necessary, but typically proceeds sufficiently well at about atmospheric pressure. The process is generally run for a time sufficient to convert as much of the carbonyl-containing compound to product as possible. Typical reaction times range from about 30 minutes to about 24 hours, but longer times may be used if necessary.

The product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of alpha-aryl product recovered, based on the number of moles of carbonyl-containing compound employed. Typically, the yield of alpha-aryl product is greater than about 25 mole percent. Preferably, the yield of alpha-aryl product is greater than about 60 mole percent, and more preferably, greater than about 80 mole percent.

The following examples are intended to illustrate, but in no way limit the scope of the present invention. All parts and percentages are by weight and all temperatures are in degrees Celsius unless explicitly stated otherwise.

EXAMPLES 1–15

The results of fifteen (15) alpha-arylation reactions are shown in Table I. As indicated in Table I, each arylation reaction was undertaken using one of seven methods, each of which is described in more detail below. Yields are for isolated pure material, and are an average of at least two runs unless explicitly stated otherwise.

Method A:

1.0 mmol of arylating compound, 1.1 mmol of carbonyl-containing compound, 5 mol % $Pd(dba)_2$, 7.5 mol % 1,1'-bis(di-o-tolylphosphino)ferrocene (DTPF), and 1.2 equivalents $KN(SiMe_3)_2$, were reacted by mixing with a magnetic stir bar at 70° C. for 2 hours. The reactions took place in tetrahydrofuran solvent, and the products were isolated by silica gel chromatograph eluting with a mixture of hexanes and ethyl acetate (EtOAc).

Method B:

Procedures are the same as Method A, except 7.5 mol % 1,1'-bis(diphenylphosphino)ferrocene (DPPF) were used instead of DTPF. Solvent and isolation procedure was the same as Method A.

Method C:

Procedures are the same as Method A, except 10 mol % $Pd(dba)_2$, and 15 mol % DPPF were used. Solvent and isolation procedure was the same as Method A.

Method D:

Procedures are the same as Method A, except 1.2 equivalents of NaO-t-Bu were used as the base. Solvent and isolation procedure was the same as Method A.

Method E:

Procedures are the same as Method A, except 2.0 mol % $Pd(OAc)_2$ and 2.2 mol % 1-di-t-butlyphosphino-2-methylaminoethyl ferrocene was used. The product was identified by gas chromatography and mass spectroscopy. Yields are estimates.

Method F:

Procedures are the same as Method A, except 2 mol % $Pd(OAc)_2$ and 2.2 mol % BINAP were used. The product was identified by gas chromatography and mass spectroscopy. Yields are estimates.

Method G:

Procedures are the same as Method A, except 42 μmols $Pd(OAc)_2$, 63 μmols tol-BINAP, and 615 μmols $KN(SiMe_3)_2$, were used. The enantioselectivity was determined using the chiral shift reagent europium tris[3-(heptafluoropropylhydroxy methylene)-(+)-camphorate].

TABLE I

Transition Metal-Catalyzed Alpha-Arylations of Carbonyl-Containing Compounds

| Example | Arylating Compound | Carbonyl Compound | Product | Method | Yield |
|---|---|---|---|---|---|
| 1 | PhBr | CH₃C(O)Ph | PhCH₂C(O)Ph | A<br>B | 84%<br>76% |
| 2 | PhBr | EtC(O)Ph | Ph(CH₃)CHC(O)Ph | A<br>B | 71%<br>47% |
| 3 | PhI | CH₃C(O)Ph | PhCH₂C(O)Ph | A | 79% |
| 4 | PhBr | iPrC(O)Ph | Ph(CH₃)₂CC(O)Ph | C<br>E | 55%<br>>90% |

TABLE I-continued

Transition Metal-Catalyzed Alpha-Arylations of Carbonyl-Containing Compounds

| Example | Arylating Compound | Carbonyl Compound | Product | Method | Yield |
|---|---|---|---|---|---|
| 5 | 2-bromotoluene | PhC(O)CH3 | 2-methylphenyl-CH2-C(O)Ph | A | 94% |
| 6 | 4-bromo-tBu-benzene | PhC(O)CH3 | 4-tBu-phenyl-CH2-C(O)Ph | A | 85% |
| 7 | 3-bromobenzonitrile | PhC(O)CH3 | 3-CN-phenyl-CH2-C(O)Ph | D | 73% |
| 8 | 4-bromoanisole | PhC(O)CH3 | 4-MeO-phenyl-CH2-C(O)Ph | A | 69% |
| 9 | PhBr | 1-methyl-2-acetylpyrrole | 1-methyl-2-(PhCH2C(O))pyrrole | A | 79% |
| 10 | PhBr | 2-acetylthiophene | 2-(PhCH2C(O))thiophene | A | 68% |
| 11 | PhBr | 2-acetylfuran | 2-(PhCH2C(O))furan | A | 57% |
| 12 | PhBr | tBuC(O)CH3 | PhCH2C(O)tBu | A | 51% |
| 13 | PhBr | tBuC(O)CH2C(O)tBu | tBuC(O)CH(Ph)C(O)tBu | F | 50–90% |
| 14 | PhBr | 2-methyl-1-indanone | 2-methyl-2-phenyl-1-indanone | A | 20% |

TABLE I-continued

Transition Metal-Catalyzed Alpha-Arylations of Carbonyl-Containing Compounds

| Example | Arylating Compound | Carbonyl Compound | Product | Method | Yield |
|---------|-------------------|-------------------|---------|--------|-------|
| 15 | 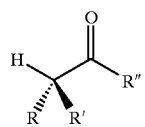 | 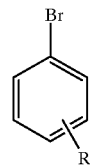 | 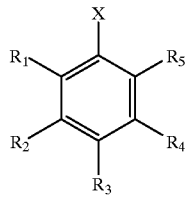 | G | 47% |

What is claimed is:

1. A process for preparing an alpha-arylated carbonyl compound, comprising the step of:
reacting a compound having at least one carbonyl group and an atom alpha to said carbonyl group bearing at least one hydrogen atom selected from the group consisting of ketones, amides, esters, carboxylic acids, thioesters, amidines, anhydrides, β-dicarbonyl compounds, and α-dicarbonyl compounds with an arylating compound in the presence of a base and a transition metal catalyst under reaction conditions effective to form said alpha-arylated carbonyl compound, said transition metal catalyst comprising a Group 8 metal and at least one chelating ligand selected from the group consisting of unsaturated Group 15 heterocycles, Group 15-substituted metallocenes, Group 15-substituted alkanes, and Group 15-substituted arylenes.

2. The process of claim 1, wherein said compound having at least one carbonyl group and an atom alpha to said carbonyl group bearing at least one hydrogen atom is selected from those having the structure where R and R' are independently selected from the group consisting of hydrogen, aryl, and alkyl; and R" is selected from the group consisting of hydrogen, aryl and alkyl.

3. The process of claim 1, wherein said compound having at least one carbonyl group and an atom alpha to said carbonyl group bearing at least one hydrogen atom is selected from the group consisting of acetophenone, propiophenone, isobutyrophenone, acetone, and diethyl ketone.

4. The process of claim 1, wherein said arylating compound is selected from those having the structure wherein X is a halogen atom or a sulfur-containing leaving group, and $R_1$, $R_2$, $R_3$, $R_4$, $R_5$ are independently selected from the group consisting of H, CN, alkyl, alkoxy, vinyl, alkenyl, formyl, $CF_3$, $CCl_3$, halide, $C_6H_5$, amide, acyl, ester, alkoxy, amino, thioalkoxy, and phosphino.

5. The process of claim 1, wherein said arylating compound is selected from those having the structure wherein R is p-CN, m-CN, p-t-Bu, m-OMe, p-OMe o-Me, p-C(O)H, p-$CF_3$, p-Ph, p-C(O)$Et_2$, p-H, and p-C(O)Ph.

6. The process of claim 1, wherein said base is selected from the group consisting of alkali metal hydroxides, alkali metal alkoxides, metal carbonates, alkali metal amides, alkali metal aryl oxides, tertiary amines, tetraalkylammonium hydroxides, diaza organic bases, and silyl.

7. The process of claim 1, wherein said Group 8 metal is selected from the group consisting of palladium, platinum, and nickel.

8. The process of claim 1, wherein said Group 15-substituted metallocene is a Group 15-substituted metallocene of iron, titanium, vanadium, chromium, manganese, cobalt, nickel, molybdenum, or ruthenium.

9. The process of claim 8, wherein said Group 15-substituted metallocene is a Group 15-substituted ferrocene.

10. The process of claim 9, wherein said Group 15-substituted ferrocene is 1,1'-bis(diphenylphosphino)ferrocene.

11. The process of claim 9, wherein said Group 15-substituted ferrocene is 1,1'-bis(di-o-tolylphosphino)ferrocene.

12. The process of claim 1, wherein said Group 15-substituted arylene is a Group 15-substituted $C_{4-20}$ arylene.

13. The process of claim 12, wherein the Group 15-substituted arylene is 1,1'-bis(diphenylphosphino)-2,2'-binaphthyl or 1,1'-bis(di-p-tolylphosphino)-2,2'-binaphthyl.

14. The process of claim 1, wherein said transition metal catalyst is selected from those having the formula

wherein (LL) is the chelating ligand, M is the Group 8 transition metal, each X is independently a monovalent or divalent anionic ligand, and wherein y varies from 0 to 4.

15. The process of claim 14, wherein the transition metal catalyst is selected from the group consisting of dichloro-[1,1'-bis(diphenylphosphino)-ferrocene]palladium (II), dichloro[1,1'-bis(di-o-tolylphosphino)ferrocene]palladium (II), dichloro-[1,1-bis(diphenylphosphino)-2,2'-binaphthyl]-palladium (II), dichloro-[1,2-bis(diphenyl-arsino)benzene] platinum (II), 1,2-bis(diphenylphos-phino)benzene) platinum (II) acetate, and dichloro-[1-diphenylphosphino-2-(1-dimethylamino) ethyl-ferrocene]palladium (II).

16. The process of claim 1, wherein the catalyst is prepared in situ in the reaction mixture.

17. The process of claim 16, wherein the catalyst is prepared from an alkene or diene complex of a Group 8 transition metal complex or a Group 8 transition metal carboxylate combined with 1,1'-bis(diphenylphosphino)ferrocene, 1,1'-bis(di-o-tolylphosphino)ferrocene, or 1,1'-bis(diphenylphosphino)-2,2-binaphthyl.

18. The process of claim 17, wherein the alkene complex of the Group 8 transition metal is di(benzylidene)acetone.

19. The process of claim 1, wherein the catalyst is anchored or supported on a catalyst support.

20. The process of claim 1, wherein said reaction conditions further comprise a solvent selected from the group consisting of aromatic hydrocarbons, chlorinated aromatic hydrocarbons, ethers, water, and aliphatic alcohols.

21. The process of claim 1, further comprising the step of isolating said alpha-arylated carbonyl compound.

22. A process for preparing an alpha-arylated carbonyl compound, comprising the step of reacting a compound having at least one carbonyl group and an atom alpha to said carbonyl group bearing at least one hydrogen atom with an arylating compound in the presence of a base and a transition metal catalyst under reaction conditions effective to form said alpha-arylated carbonyl compound, said transition metal catalyst selected from the group consisting of dichloro [1,1'-bis(diphenylphosphino)-ferrocene]palladium (II), and dichloro[1,1'-bis(di-o-tolylphosphino)ferrocene]palladium (II),.

* * * * *